United States Patent [19]
Torii et al.

[11] Patent Number: 4,566,996
[45] Date of Patent: Jan. 28, 1986

[54] PROCESS FOR PREPARING AZETIDINONE DERIVATIVES

[75] Inventors: Sigeru Torii; Hideo Tanaka, both of Okayama; Takashi Shiroi, Tokushima; Michio Sasaoka, Tokushima; Norio Saito, Tokushima; Kiyotoshi Matsumura, Tokushima, all of Japan

[73] Assignee: Otsuke Kagaku Yakuhin Kabushiki Kaisha, Japan

[21] Appl. No.: 567,736

[22] Filed: Jan. 3, 1984

[30] Foreign Application Priority Data

Jan. 19, 1983 [JP] Japan .................................. 58-7630

[51] Int. Cl.$^4$ .................. C07D 205/08; C07D 405/12
[52] U.S. Cl. .............................. 260/239 A; 260/330.9
[58] Field of Search ...................... 260/239 AL, 330.9

[56] References Cited

U.S. PATENT DOCUMENTS 4,319,027 3/1982 Woodward ..................... 260/239 A
4,332,722 6/1982 Tsuji et al. ..................... 260/239 A

OTHER PUBLICATIONS

Sedelmeier et al., Chem. Abs. 98, 197883t.

Primary Examiner—Mark L. Berch
Attorney, Agent, or Firm—Larson and Taylor

[57] ABSTRACT

A process for preparing an azetidinone derivative represented by the formula (1)

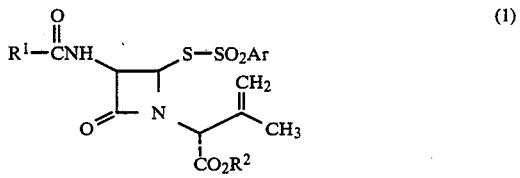

wherein $R^1$ represents a substituted or unsubstituted aryl group, a substituted or unsubstituted phenylmethyl group or a substituted or unsubstituted phenoxymethyl group, $R^2$ represents a hydrogen atom or a group for protecting carboxylic acid and Ar represents a substituted or unsubstituted phenyl group, the process comprising reacting a thiazolineazetidinone derivative represented by the formula (2)

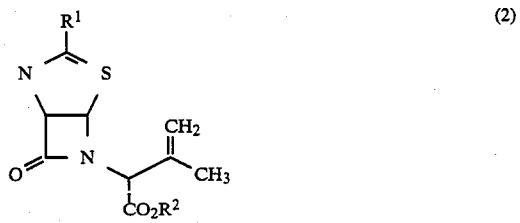

wherein $R^1$ and $R^2$ are as defined above with a sulfonyl bromide represented by the formula (3)

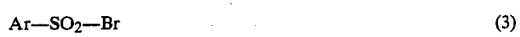

wherein Ar is as defined above in water-containing organic solvent.

8 Claims, No Drawings

PROCESS FOR PREPARING AZETIDINONE DERIVATIVES

The present invention relates to a process for preparing azetidinone derivatives, and more particularly to a process for preparing azetidinone derivatives represented by the formula

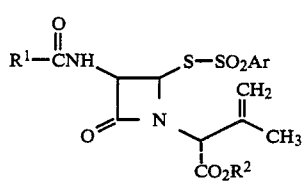
(1)

wherein $R^1$ represents a substituted or unsubstituted aryl group, a substituted or unsubstituted phenylmethyl group or a substituted or unsubstituted phenoxymethyl group, $R^2$ represents a hydrogen atom or a group for protecting carboxylic acid and Ar represents a substituted or unsubstituted phenyl group.

The azetidinone derivatives of the formula (1) which can be prepared according to the present invention are important intermediates for synthesizing cephalosporin-type antibiotics, and can be converted into cephalosporin derivatives, for example, as shown below in Reaction Equation (A) according to a process disclosed in Tetrahedron Letters 1982, 23, 2187.

Reaction Equation (A)

In Reaction Equation (A), $R^1$, $R^2$ and Ar are as defined above.

The azetidinone derivatives of the formula (1) have been conventionally synthesized, for example, by processes as shown below in Reaction Equation (B) disclosed in J. Gosteli, Chimica, 30, 13 (1976) and Reaction Equation (C) described in R. D. Allan, D. H. R. Barton, M. Girizavallabhan and P. G. Sammes, J. Chem. Soc., Perkin I, 1456 (1974).

Reaction Equation (B)

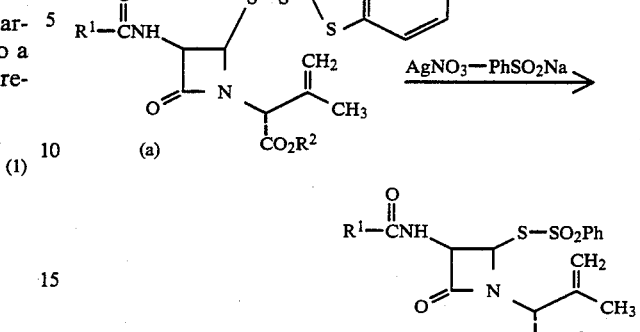

Reaction Equation (C)

In Reaction Equations (B) and (C), Ph represents a phenyl group and $R^1$ and $R^2$ are as defined above.

However, the processes of Reaction Equations (B) and (C) are commercially disadvantageous because of the following serious drawbacks. The process of Reaction (B) entails the problems of using an expensive silver compound in large amounts and producing by-products which are difficult to separate. And the process of Reaction Equation (C) gives a considerable amount of a by-product (d), consequently producing the azetidinone derivative of the formula (1) [the compound indicated as (b) in Reaction Equations (B) and (C)] in a low yield of about 20%.

It is an object of the present invention to provide a novel process for preparing an azetidinone derivative of the formula (1) which is free from the foregoing drawbacks.

It is another object of the present invention to provide a process for preparing an azetidinone derivative of the formula (1) from easily available starting compounds without using an expensive silver compound.

It is a further object of the invention to provide a process for preparing an azetidinone derivative of the formula (1) with a high purity of as high as nearly 100% in a high yield.

Other features of the present invention will become apparent from the following description.

The present invention provides a process for preparing an azetidinone derivative represented by the formula (1) comprising reacting a thiazoline-azetidinone derivative represented by the formula (2)

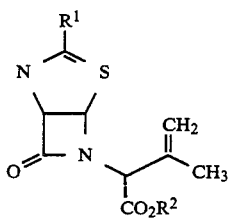

wherein $R^1$ and $R^2$ are as defined above with a sulfonyl bromide represented by the formula (3)

$$Ar-SO_2-Br \qquad (3)$$

wherein Ar is as defined above.

The process of the present invention requires no expensive silver compound and gives the compound of the formula (1) free from any position isomer [the compound represented by (d) in Reaction Equation (C)] and thus with a high purity in a high yield. The present process is also advantageous in that the compound (2) to be used as the starting material is readily prepared from penicillin-S-oxide [the compound (4) in the following reaction scheme] by a conventional process [reported, for example, in R. D. G. Cooper and F. L. Jase, J. Am. Chem. Soc., 92, 2575 1970] as shown in the reaction scheme given below, whereby the compound of the formula (1) can be manufactured at lower cost.

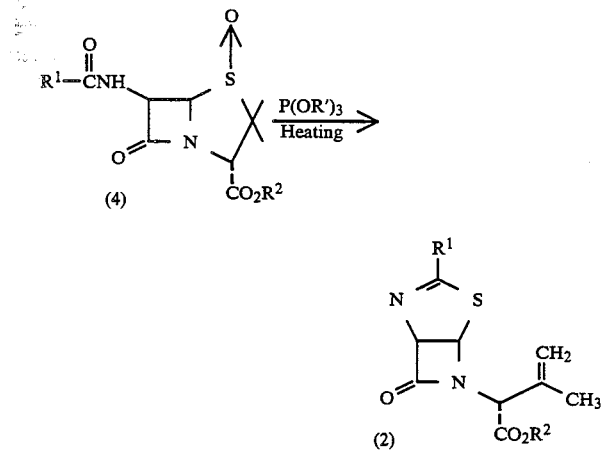

In the above reaction scheme, R' represents a lower alkyl group, and $R^1$ and $R^2$ are as defined above.

The kinds of groups $R^1$ and $R^2$ in the thiazolineazetidinone derivative of the formula (1) to be used as a starting material in the present process are not particularly limited and include an amino-protecting group and a group for protecting carboxylic acid which are commonly used in the reaction for the conversion of penicillin to cephalosporin. Examples of the groups $R^1$ are phenyl, p-nitrophenyl, p-chlorophenyl and like substituted or unsubstituted aryl groups; phenylmethyl, p-nitrophenylmethyl, p-chlorophenylmethyl, diphenylmethyl, phenyldichloromethyl, phenylhydroxymethyl and like substituted or unsubstituted phenylmethyl groups; phenoxymethyl, p-chlorophenoxymethyl, p-methoxyphenoxymethyl and like substituted or unsubstituted phenoxymethyl groups, etc. Examples of the groups $R^2$ are benzyl, p-methoxybenzyl, trimethoxybenzyl, trimethoxydichlorobenzyl, piperonyl, diphenylmethyl, bis(p-methoxyphenyl)methyl, ditolylmethyl, phenyl-p-methoxyphenylmethyl, α-p-methoxyphenylethyl, α-p-methoxyphenyl-β-trichloroethyl, trichloroethyl, fluorenyl, methyl, ethyl, propyl, tert-butyl, trityl, α-diphenylethyl, cumyl, p-nitrobenzyl, o-nitrobenzyl, o,p-dinitrobenzyl, phenacyl, p-bromophenacyl, 1-methoxycarbonyl-2-oxopropyl, methoxyethoxymethyl, methoxymethyl, benzyloxymethyl, isopropoxymethyl, etc.

Examples of the groups Ar in the sulfonyl bromide represented by the formula (3) are phenyl, p-methylphenyl, p-chlorophenyl, p-nitrophenyl, p-methoxyphenyl, 2,4-dinitrophenyl and like substituted or unsubstituted phenyl groups, etc.

According to the present invention, the thiazolineazetidinone derivative of the formula (2) and sulfonyl bromide of the formula (3) are subjected to reaction in a water-containing organic solvent preferably in the presence of an acid. A preferred embodiment of the present process is as follows. The thiazolineazetidinone derivative of the formula (2) is dissolved in an organic solvent to provide a solution of about 1 mole/l to about 0.01 mole/l of the thiazolineazetidinone derivative of the formula (2). To the solution are added an aqueous solution of an acid and a sulfonyl bromide of the formula (3) for reaction. The reaction temperature and the reaction time vary depending on the kinds of the thiazolineazetidinone derivative of the formula (2), sulfonyl bromide of the formula (3), acid and solvent to be used. The reaction is conducted at a temperature ranging usually from about −20° to about 50° C., preferably about 0° to about 20° C. and is completed usually in 10 minutes to 2 hours. While the reaction can be performed by adding the acid and the sulfonyl bromide of the formula (3) at the same time, the acid may be added first to continue reaction for about 5 minutes to about 5 hours and then the sulfonyl bromide of the formula (3) may be added to complete reaction. The amount of the sulfonyl bromide of the formula (3) to be used is not particularly limited and can be suitably determined over a wide range. Usually about 1 to about 5 moles, preferably about 1 to about 1.2 moles, of the sulfonyl bromide of the formula (3) is used per mole of the thiazolineazetidinone derivative of the formula (2). Useful acids include mineral acids and organic acids as widely used heretofore in the art, such as hydrochloric acid, sulfuric acid, nitric acid, perchloric acid and like mineral acids and acetic acid, formic acid, trifluoroacetic acid and like organic acids. Among them, preferably an about 1 to about 20% aqueous solution of hydrochloric acid or an about 1 to about 20% aqueous solution of perchloric acid is used. The amount of the acid to be used is not particularly limitative and can be appropriately selected over a wide range. Usually about 0.1 to about 10 moles, preferably about 1 to about 1.5 moles of the acid is used per mole of the thiazolineazetidinone derivative of the formula (2).

Useful organic solvents include hydrophilic solvents and they are used singly or in mixture with each other. Examples of the hydrophilic solvents are methanol, ethanol, isopropanol and like lower alcohols, acetone, ethyl methyl ketone and like ketones; acetonitrile, butyronitrile and like nitriles; diethyl ether, dibutyl ether, testrahydrofuran, dioxane and like ethers; nitromethane, nitroethane and like lower nitroparaffins, etc. Hydrophic organic solvents are also used as mixed with the hydrophilic solvent. Examples of useful hydrophobic solvents are dichloromethane, 1,2-dichloroethane, chloroform, carbon tetrachloride, benzene, chlorobenzene, ethyl acetate, ethyl formate, etc.

According to this invention, water is present in the reaction system in an amount of at least about 1 mole per mole of the thiazolineazetidinone derivative of the formula (2).

Examples of the groups $R^1$, $R^2$ and Ar in the compound of the formula (1) thus obtained are the same as those exemplified above in respect of the compounds of the formula (2) and (3).

The reaction product thus obtained is easily isolated and purified by the conventional separation method, such as silica gel column chromatography.

The present invention will be described below in more detail with reference to the following Examples.

EXAMPLE 1

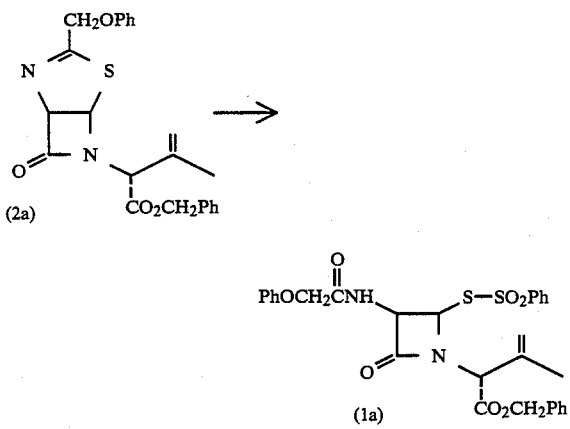

A 403 mg (0.95 mmol) quantity of benzyl 2-(3-phenoxymethyl-7-oxo-4-thia-2,6-diazabicyclo[3,2,0-]hepto-2-ene-6-yl)-3-methyl-3-butenoate (2a) was weighed out and 12 ml of methanol was added to form a uniform solution. To the solution was added with ice-cooling 1.1 ml of 1N—HCl and the mixture was stirred at 10° to 15° C. for 4 hours. To the reaction mixture was added 232 mg (1.05 mmol) of benzene sulfonyl bromide and the mixture was agitated at 10° to 15° C. for 30 minutes. To the reaction mixture was added a saturated aqueous solution of sodium chloride and the mixture was extracted twice with ethyl acetate (30 ml). The extracts were washed with a saturated aqueous solution of sodium chloride, dried over MgSO4 and concentrated at reduced pressure. The residue was subjected to silica gel column chromatography using benzene/ethyl acetate (9:1), giving 514 mg of benzyl 2-(3-phenoxyacetamido-4-benzenesulfonylthio-2-azetidinone-1-yl)-3-methyl-butenoate (1a) in a yield of 93%. Table III below shows the spectrum data of the compound of the formula (1a) thus obtained.

EXAMPLES 2 TO 7

The same procedure as in Example 1 was repeated with the exception of using the solvents shown in Table I below, producing the compound of the formula (1a).

TABLE I

| Example | Solvent | Yield (%) |
|---|---|---|
| 2 | Acetone | 76 |
| 3 | Tetrahydrofuran | 60 |
| 4 | Acetone-CH2Cl2 (1/1) | 35 |
| 5 | Tetrahydrofuran-CH2Cl2 (1/1) | 56 |
| 6 | Ethanol | 75 |
| 7 | Isopropanol | 65 |

EXAMPLE 8

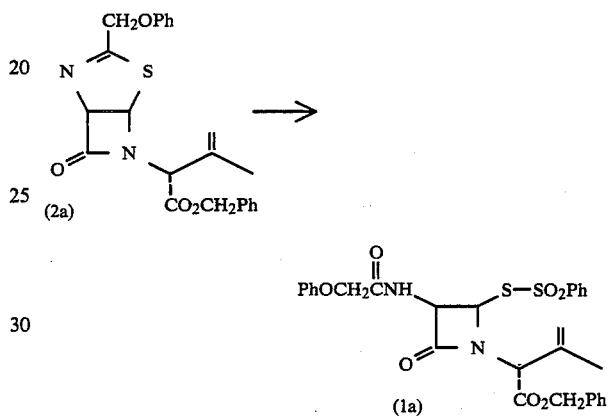

A 347 mg (0.82 mmol) quantity of benzyl 2-(3-phenoxymethyl-7-oxo-4-thia-2,6-diazabicyclo[3,2,0-]hepto-2-ene-6-yl)-3-methyl-3-butenoate (2a) was dissolved in 10 ml of methanol to obtain a uniform solution. To the solution were added with ice-cooling 1 ml of 1N—HCl and 232 mg (1.05 mmol) of benzene sulfonyl bromide at the same time and the mixture was stirred at 10° to 15° C. for 4.5 hours. The reaction mixture was treated in the same manner as in Example 1, affording 373 mg of benzyl 2-(3-phenoxyacetamido-4-benzenesulfonylthio-2-azetidinone-1-yl)-3-methyl-butenoate (1a) in 78% yield.

The results of the spectrum data obtained in respect of the product were identical with those of the product produced in Example 1.

EXAMPLES 9 TO 21

The procedure of Example 1 was repeated with the exception of using the thiazolineazetidinone derivatives of the formula (2), aryl sulfonyl bromides of the formula (3), solvents and acids indicated in Table II below, giving compounds of the formula (1). Table III below shows the spectrum data in respect of the compounds of the formula (1) thus obtained.

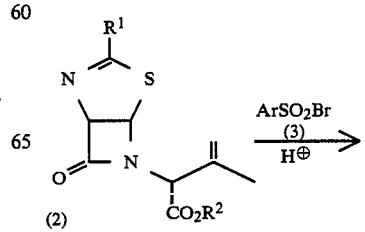

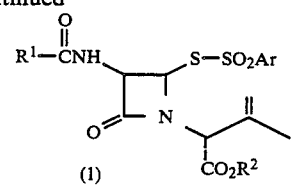

TABLE II

| Example No. | Compound (2) R¹ | R² | Compound (3) Ar | Acid/Solvent | Yield (%) |
|---|---|---|---|---|---|
| 9 | PhOCH$_2$ | PhCH$_2$ | p-CH$_3$—Ph | 1N—HCl/Methanol | 77 |
| 10 | PhOCH$_2$ | CH$_3$ | Ph | 5% HClO$_4$/THF-Methanol (1:1) | 65 |
| 11 | PhCH$_2$ | CH$_3$ | Ph | 1N—HCl/Methanol | 85 |
| 12 | PhCH$_2$ | CH$_3$ | p-Cl—Ph | 1N—HCl/Methanol | 87 |
| 13 | PhCH$_2$ | CH$_3$ | p-NO$_2$—Ph | 1N—HCl/Methanol | 78 |
| 14 | PhCH$_2$ | CH$_3$ | o-NO$_2$—Ph | 1N—HCl/Methanol | 82 |
| 15 | PhCH$_2$ | CH$_3$ | p-CH$_3$—Ph | 1N—HCl/Methanol | 90 |
| 16 | PhOCH$_2$ | PhCH$_2$ | p-NO$_2$—Ph | 1N—HCl/Methanol | 92 |
| 17 | PhCH$_2$ | PhCH$_2$ | Ph | 1N—HCl/Methanol-THF (1:1) | 80 |
| 18 | PhCH$_2$ | PhCH$_2$ | p-NO$_2$—Ph | 1N—HCl/Methanol | 85 |
| 19 | PhCH$_2$ | PhCH$_2$ | p-CH$_3$O—Ph | 1N—HCl/Methanol | 82 |
| 20 | PhCH$_2$ | p-NO$_2$—PhCH$_2$ | p-NO$_2$—Ph | 1N—HCl/Methanol | 78 |
| 21 | PhCH$_2$ | Cl$_3$CCH$_2$ | p-NO$_2$—Ph | 1N—HCl/Methanol | 85 |

Ph: Phenyl
p-: para
o-: ortho
THF: Tetrahydrofuran

TABLE III

| Example No. | Compound (1) | $^1$HNMR (CDCl$_3$) δ (ppm) | m/e |
|---|---|---|---|
| 1 | R¹ = PhOCH$_2$<br>R² = PhCH$_2$<br>Ar = Ph | 1.79 (3H, s), 4.42 (2H, s),<br>4.45 (2H, broad s), 4.83 (1H, s),<br>5.17 (2H, s), 5.25 (1H, dd, J = 5 and 8Hz),<br>5.90 (1H, d, J = 5Hz), 6.94 (1H, d, J = 8Hz),<br>7.20–7.78 (15H, m) | 581 (M$^+$ + 1) |
| 9 | R¹ = PhOCH$_2$<br>R² = PhCH$_2$<br>Ar = p-CH$_3$Ph | 1.80 (3H, s), 2.38 (3H, s), 4.39 (2H, s),<br>4.44 (2H, broad s), 4.83 (1H, s),<br>5.18 (2H, s), 5.30 (1H, dd, J = 5 and 8Hz),<br>5.86 (1H, d, J = 5Hz), 6.93 (1H, d, J = 8Hz),<br>7.20–7.78 (14H, m) | 595 (M$^+$ + 1) |
| 10 | R¹ = PhOCH$_2$<br>R² = CH$_3$<br>Ar = Ph | 1.80 (3H, s), 3.72 (3H, s), 4.41 (2H, s),<br>4.61 (1H, broad s), 4.80 (1H, s),<br>4.88 (1H, broad s),<br>5.30 (1H, dd, J = 5 and 8Hz),<br>5.91 (1H, d, J = 5Hz), 6.8–8.0 (11H, m) | 505 (M$^+$ + 1) |
| 11 | R¹ = PhCH$_2$<br>R² = CH$_3$<br>Ar = Ph | 1.77 (3H, s), 3.50 (2H, s), 3.68 (3H, s),<br>4.58 (1H, broad s), 4.74 (1H, s),<br>4.83 (1H, broad s),<br>5.10 (1H, dd, J = 5 and 8Hz),<br>5.80 (1H, d, J = 5Hz), 6.50 (1H, d, J = 8Hz),<br>7.26 (5H, s), 7.3–8.0 (5H, m) | 489 (M$^+$ + 1) |
| 12 | R¹ = PhCH$_2$<br>R² = CH$_3$<br>Ar = p-Cl—Ph | 1.78 (3H, s), 3.51 (2H, broad s), 3.70 (3H, s),<br>4.61 (1H, broad s), 4.76 (1H, s),<br>4.86 (1H, broad s), 5.06 (1H, dd, J = 5 and 8Hz),<br>5.83 (1H, d, J = 5Hz), 7.14 (1H, d, J = 8Hz),<br>7.23 (5H, s), 7.43 (2H, d, J = 8Hz),<br>7.81 (2H, d, J = 8Hz) | 523 (M$^+$ + 1) |
| 13 | R¹ = PhCH$_2$<br>R² = CH$_3$<br>Ar = p-NO$_2$—Ph | 1.80 (3H, s), 3.52 (2H, broad s), 3.70 (3H, s),<br>4.55 (1H, broad s), 4.79 (1H, s),<br>4.87 (1H, broad s), 5.03 (1H, dd, J = 5 and 8Hz),<br>5.87 (1H, d, J = 5Hz), 6.73 (1H, d, J = 8Hz),<br>7.22 (5H, s), 7.94 (2H, d, J = 9Hz),<br>8.24 (2H, d, J = 9Hz) | 534 (M$^+$ + 1) |
| 14 | R¹ = PhCH$_2$<br>R² = CH$_3$<br>Ar = o-NO$_2$—Ph | 1.80 (3H, s), 3.48 (2H, broad s), 3.70 (3H, s),<br>4.64 (1H, broad s), 4.80 (1H, s),<br>4.88 (1H, broad s), 5.13 (1H, dd, J = 5 and 8Hz),<br>6.06 (1H, d, J = 5Hz), 6.88 (1H, d, J = 8Hz),<br>7.17 (5H, s), 7.6–8.2 (4H, m) | 534 (M$^+$ + 1) |
| 15 | R¹ = PhCH$_2$<br>R² = CH$_3$<br>Ar = p-CH$_3$—Ph | 1.74 (3H, s), 2.40 (3H, s), 3.50 (2H, s),<br>3.71 (3H, s), 4.64 (1H, s), 4.70 (1H, s),<br>4.89 (1H, s), 5.05 (1H, dd, J = 5 and 8Hz),<br>5.78 (1H, d, J = 5Hz), 6.52 (1H, d, J = 8Hz),<br>7.22 (5H, s), 7.30 (2H, d, J = 9Hz), | 503 (M$^+$ + 1) |

TABLE III-continued

| Example No. | Compound (1) | $^1$HNMR (CDCl$_3$) δ (ppm) | m/e |
|---|---|---|---|
| 16 | R$^1$ = PhOCH$_2$<br>R$^2$ = PhCH$_2$<br>Ar = p-NO$_2$—Ph | 7.68 (2H, d, J = 9Hz)<br>1.80 (3H, s), 4.45 (2H, broad s),<br>4.78 (1H, broad s), 4.93 (1H, s),<br>5.15 (3H, s), 5.22 (1H, dd, J = 5 and 8Hz),<br>6.07 (1H, d, J = 5Hz), 6.7–7.5 (5H, m),<br>7.32 (5H, s), 7.62 (1H, d, J = 8Hz),<br>7.94 (2H, d, J = 9Hz), 8.16 (2H, d, J = 9Hz) | 626 (M$^+$ + 1) |
| 17 | R$^1$ = PhCH$_2$<br>R$^2$ = PhCH$_2$<br>Ar = Ph | 1.73 (3H, s), 3.53 (2H, s), 4.50 (1H, broad s),<br>4.78 (2H, broad s), 5.09 (1H, dd, J = 5 and 8Hz),<br>5.12 (2H, s), 5.78 (1H, d, J = 5Hz),<br>6.36 (1H, d, J = 8Hz), 7.24 (5H, s),<br>7.30 (5H, s), 7.30–7.90 (5H, m) | 565 (M$^+$ + 1) |
| 18 | R$^1$ = PhCH$_2$<br>R$^2$ = PhCH$_2$<br>Ar = p-NO$_2$—Ph | 1.75 (3H, s), 3.50 (2H, s), 4.76 (1H, broad s),<br>4.84 (1H, s), 4.92 (1H, broad s),<br>5.10 (1H, dd, J = 5 and 8Hz), 5.12 (2H, s),<br>5.92 (1H, d, J = 5Hz), 6.91 (1H, d, J = 8Hz),<br>7.20 (5H, s), 7.30 (5H, s),<br>7.87 (2H, d, J = 9Hz), 8.18 (2H, d, J = 9Hz) | 610 (M$^+$ + 1) |
| 19 | R$^1$ = PhCH$_2$<br>R$^2$ = PhCh$_2$<br>Ar = p-CH$_3$O—Ph | 1.75 (3H, s), 3.50 (2H, s), 3.79 (3H, s),<br>4.65 (1H, broad s), 4.77 (1H, s),<br>4.85 (1H, broad s), 5.12 (1H, dd, J = 5 and 8Hz),<br>5.13 (2H, s), 5.73 (1H, d, J = 5Hz),<br>6.63 (1H, d, J = 8Hz), 6.87 (2H, d, J = 9Hz),<br>7.20 (5H, s), 7.29 (5H, s), 7.67 (2H, d, J = 9Hz) | 595 (M$^+$ + 1) |
| 20 | R$^1$ = PhCH$_2$<br>R$^2$ = p-NO$_2$—Ph<br>Ar = p-NO$_2$—Ph | 1.81 (3H, s), 3.50 (2H, s), 4.59 (1H, broad s),<br>4.85 (2H, broad s), 5.02 (1H, dd, J = 5 and 7Hz),<br>5.21 (2H, s), 5.86 (1H, d, J = 5Hz),<br>6.90 (1H, d, J = 7Hz), 7.20 (5H, s),<br>7.45 (2H, d, J = 8.5Hz), 7.91 (2H, d, J = 9Hz),<br>8.10 (2H, d, J = 8.5Hz), 8.20 (2H, d, J = 9Hz) | 641 (M$^+$ + 1) |
| 21 | R$^1$ = PhCH$_2$<br>R$^2$ = CCl$_3$CH$_2$<br>Ar = p-NO$_2$—Ph | 1.83 (3H, s), 3.50 (2H, s), 4.73 (1H, s),<br>4.78 (2H, s), 4.95 (1H, s), 4.97 (1H, s),<br>5.09 (1H, dd, J = 5 and 8Hz),<br>5.84 (1H, d, J = 5Hz), 6.79 (1H, d, J = 8Hz),<br>7.24 (5H, s), 7.93 (2H, d, J = 9Hz),<br>8.26 (2H, d, J = 9Hz) | 650 (M$^+$ + 1) |

EXAMPLE 22

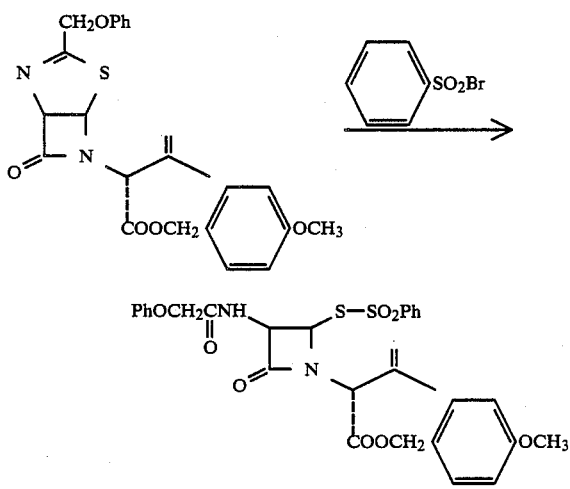

There was dissolved in 12 ml of methanol 400 mg of p-methoxybenzyl 2-(3-phenoxymethyl-7-oxo-4-thia-2,6-diazabicyclo[3,2,0]hepto-2-ene-6-yl)-3-methyl butenoate to obtain a uniform solution. To the solution was added 1.1 ml of 1N—HCl with ice-cooling and the mixture was agitated at 10° to 15° C. for 4 hours. To the reaction mixture was added 210 mg of benzene sulfonyl bromide and the mixture was agitated at 10° to 15° C. for 30 minutes. To the reaction mixture was added a saturated aqueous solution of sodium chloride and the mixture was extracted twice with ethyl acetate (30 ml×2). The extracts were washed with a saturated aqueous solution of sodium chloride, dried over MgSO$_4$ and concentrated at reduced pressure. The residue was subjected to silica gel column chromatography using benzene/ethyl acetate (9:1), giving 480 mg of p-methoxybenzyl 2-(3-phenoxyacetamido-4-benzenesulfonylthio-2-azetidinone-1-yl)-3-methyl-3-butenoate (1a) in a yield of 89%.

The NMR data obtained in respect of the compound thus produced are shown below.

NMR (δ, ppm): 1.76 (s, 3H), 3.77 (s, 3H), 4.34 and 4.40 (ABq, 2H, J=12.0 Hz), 4.53 (s, 1H), 4.76 (s, 1H), 4.79 (bs, 1H), 5.07 (s, 2H), 5.27 (dd, 1H, J=4.0 and 6.5 Hz), 5.86 (d, 1H, J=4.0 Hz), 6.65–7.90 (m, 15H).

EXAMPLES 23 TO 33

The procedure of Example 22 was repeated with the exception of using the corresponding starting compounds, producing compounds as shown in Table IV below.

TABLE IV

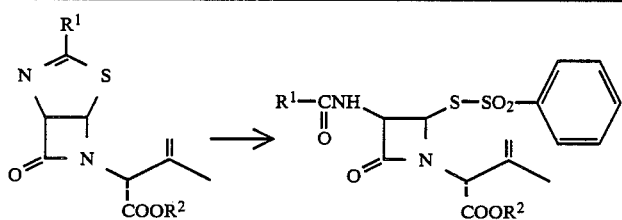

| Example No. | R¹ | R² | NMR (δ, ppm) | Yield (%) |
|---|---|---|---|---|
| 23 | PhCH₂— | —CH₂—(2-NO₂-C₆H₄) | 1.78 (s, 3H), 3.56 (s, 2H), 4.60 (s, 1H), 4.76 (s, 1H), 4.87 (bs, 1H), 5.12 (dd, 1H, J = 4.0 and 6.5Hz), 5.53 (s, 2H), 5.64 (d, 1H, J = 4.0Hz), 6.20 (d, 1H, J = 6.5Hz), 7.10–8.20 (m, 14H) | 82 |
| 24 | PhCH₂— | —CH₂—(4-NO₂-C₆H₄) | 1.78 (s, 3H), 3.56 (s, 2H), 4.57 (s, 1H), 4.76 (s, 1H), 4.88 (bs, 1H), 5.11 (dd, 1H, J = 4.0 and 7.0Hz), 5.23 (s, 2H), 5.72 (d, 1H, J = 4.0Hz), 6.06 (d, 1H, J = 7.0Hz), 7.00–8.00 (m, 12H), 8.19 (d, 2H, J = 7.0Hz) | 81 |
| 25 | PhCH₂— | —CH₂—(4-OCH₃-C₆H₄) | 1.71 (s, 3H), 3.54 (s, 2H), 3.78 (s, 3H), 4.45 (s, 1H), 4.69 (s, 1H), 4.72 (bs, 1H), 5.02 (s, 1H), 5.06 (dd, 1H, J = 4.0 and 6.5Hz), 5.70 (d, 1H, J = 4.0), 5.90 (d, 1H, J = 6.5Hz), 6.82 (d, 2H, J = 7.0Hz), 7.00–7.85 (m, 12H) | 88 |
| 26 | PhCH₂— | 9-fluorenyl | 1.76 (s, 3H), 3.57 (s, 2H), 4.71 (s, 1H), 4.82 (s, 1H), 4.84 (s, 1H), 5.16 (dd, 1H, J = 4.7 and 8.1Hz), 5.76 (d, 1H, J = 4.7Hz), 6.50 (d, 1H, J = 8.1Hz), 6.74 (s, 1H), 7.05–7.90 (m, 18H) | 86 |
| 27 | PhOCH₂— | 9-fluorenyl | 1.78 (s, 3H), 4.39 and 4.44 (ABq, 2H, J = 12.0Hz), 4.76 (s, 1H), 4.85 (s, 1H), 4.88 (bs, 1H), 5.34 (dd, 1H, J = 4.7 and 8.2Hz), 5.87 (d, 1H, J = 4.7Hz), 6.76 (s, 1H), 6.80–7.90 (m, 19H) | 88 |
| 28 | PhOCH₂— | —CH₂OCH₂CH₂OCH₃ | 1.82 (s, 3H), 3.36 (s, 3H), 3.40–3.65 (m, 2H), 3.65–3.90 (m, 2H), 4.36 and 4.41 (ABq, 2H, J = 12.0Hz), 4.69 (s, 1H), 4.79 (s, 1H), 4.94 (bs, 1H), 5.15–5.60 (m, 3H), 5.90 (d, 1H, J = 4.0Hz), 6.75–8.00 (m, 11H) | 82 |
| 29 | PhOCH₂— | —CH₂OCH₃ | 1.85 (s, 3H), 3.46 (s, 3H), 4.41 and 4.46 (ABq, 2H, J = 12.0Hz), 4.71 (s, 1H), 4.82 (s, 1H), 4.95 (bs, 1H), 5.10–5.40 (m, 3H), 5.91 (d, 1H, J = 4.7Hz), 6.80–8.00 (m, 11H) | 48 |

TABLE IV-continued

| Example No. | R¹ | R² | NMR (δ, ppm) | Yield (%) |
|---|---|---|---|---|
| 30 | PhOCH₂— | −CH(COCH₃)(COCH₃) | 1.84 (s, 3H), 2.35 (s, 3H), 3.83 (s, 3H), 4.38 and 4.45 (ABq, 2H, J = 11Hz), 4.80–5.05 (m, 3H), 5.38 (dd, 1H, J = 4.0 and 7.0Hz), 5.55 (s, 1H), 5.85 (d, 1H, J = 4.0Hz), 6.75–8.00 (m, 11H) | 86 |
| 31 | PhOCH₂— | −CH₂−(3,4,5-triOCH₃-C₆H₂) | 1.79 (s, 3H), 3.85 (s, 9H), 4.35 and 4.41 (ABq, 2H, J = 12.5Hz), 4.62 (s, 1H), 4.80 (s, 1H), 4.84 (bs, 1H), 5.08 (s, 2H), 5.26 (dd, 1H, J = 4.0 and 7.0Hz), 5.84 (d, 1H, J = 4.0Hz), 6.54 (s, 2H), 6.75–7.90 (m, 11H) | 90 |
| 32 | PhOCH₂— | −CH₂−(3,5-diCl-2,4,6-triOCH₃-C₆H) | 1.76 (s, 3H), 3.89 (s, 6H), 3.94 (s, 3H), 4.36 and 4.41 (ABq, 2H, J = 12.0Hz), 4.60 (s, 1H), 4.78 (bs, 1H), 4.80 (s, 1H), 5.24 (dd, 1H, J = 4.0 and 6.5Hz), 5.38 (s, 2H), 5.82 (s, 2H), 6.75–7.90 (m, 11H) | 81 |
| 33 | PhOCH₂— | −CH₂C(O)−C₆H₄−Br | 1.85 (s, 3H), 4.38 and 4.44 (ABq, 2H, J = 12.0Hz), 4.90 (s, 1H), 4.96 (s, 2H), 5.28 and 5.34 (ABq, 2H, J = 12.0Hz), 5.35 (dd, 1H, J = 4.0 and 6.5Hz), 5.85 (d, 1H, J = 4.0Hz), 6.75–7.95 (m, 15H) | 85 |

We claim:

1. A process for preparing an azetidinone derivative represented by the formula

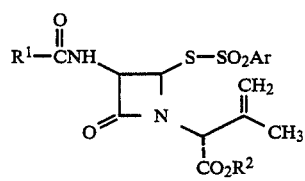

(1)

wherein R¹ represents phenyl, p-nitrophenyl, p-chlorophenyl, phenylmethyl, p-nitrophenylmethyl, p-chlorophenylmethyl, diphenylmethyl, phenyldichloromethyl, phenylhydroxymethyl, phenoxymethyl, p-chlorophenoxymethyl or p-methoxyphenoxymethyl, R² represents a hydrogen atom or a group for protecting carboxylic acid, and Ar represents phenyl, p-methylphenyl, p-chlorophenyl, p-nitrophenyl, p-methoxyphenyl or 2,4-dinitrophenyl, the process comprising reacting a thiazolineazetidinone derivative represented by the formula

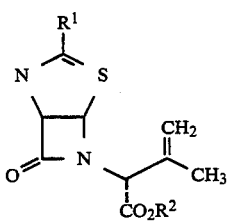

(2)

wherein R¹ and R² are as defined above with a sulfonyl bromide represented by the formula

(3)

wherein Ar is as defined above in water-containing organic solvent.

2. A process as defined in claim 1 in which the reaction is carried out in the presence of an acid.

3. A process as defined in claim 2 in which the acid is hydrochloric acid, sulfuric acid, nitric acid, perchloric acid, or acetic acid, formic acid, trifluoroacetic acid.

4. A process as defined in claim 1 in which the organic solvent is a hydrophilic organic solvent as singly used or as admixed with a hydrophobic organic solvent.

5. A process as defined in claim 1 in which the sulfonyl bromide of the formula (3) is used in an amount of about 1 to about 5 moles per mole of the thiazolineazetidinone derivative of the formula (2).

6. A process as defined in claim 1 in which the reaction is conducted at a temperature of about −20° to about 50° C.

7. A process as defined in claim 1 in which water is present in the reaction system in an amount of at least about 1 mole per mole of the thiazolineazetidinone derivative of the formula (2).

8. A process as defined in claim 1 wherein $R^2$ represents hydrogen, benzyl, p-methoxybenzyl, trimethoxybenzyl, trimethoxydichlorobenzyl, piperonyl, diphenylmethyl, bis(p-methoxyphenyl)methyl, ditolylmethyl, phenyl-p-methoxyphenylmethyl, α-p-methoxyphenylethyl, α-p-methoxyphenyl-β-trichloroethyl, trichloroethyl, fluorenyl, methyl, ethyl, propyl, tert-butyl, trityl, α-diphenylethyl, cumyl, p-nitrobenzyl, o-nitrobenzyl, o,p-dinitrobenzyl, phenacyl, p-bromophenacyl, 1-methoxycarbonyl-2-oxopropyl, methoxyethoxymethyl, methoxymethyl, benzyloxymethyl or isopropoxymethyl.

* * * * *